United States Patent [19]
Collins et al.

[11] 3,987,005
[45] Oct. 19, 1976

[54] ORGANOTIN COMPOUNDS

[75] Inventors: John Desmond Collins, Albrighton;
Iftikhar Hussain Siddiqui,
Edgbaston, both of England

[73] Assignee: Albright & Wilson Limited, Warley,
England

[22] Filed: Dec. 17, 1974

[21] Appl. No.: 533,651

[30] Foreign Application Priority Data
Dec. 18, 1973 United Kingdom............... 58577/73

[52] U.S. Cl.......................... 260/45.75 S; 260/429.7
[51] Int. Cl.² ..................... C08G 6/00; C07F 7/22
[58] Field of Search ................. 260/429.7, 45.75 K, 260/45.75 S

[56] References Cited
UNITED STATES PATENTS

| | | | |
|---|---|---|---|
| 3,078,290 | 2/1963 | Hechenbleikner et al....... | 260/429.7 |
| 3,196,129 | 7/1965 | Hechenbleikner et al... | 260/429.7 X |
| 3,209,017 | 7/1965 | Hechenbleikner et al....... | 260/429.7 |
| 3,217,004 | 11/1965 | Hechenbleikner et al....... | 260/429.7 |
| 3,640,950 | 2/1972 | Weisfeld ..................... | 260/45.75 K |
| 3,845,017 | 10/1974 | Collins et al................. | 260/45.75 K |
| 3,894,989 | 7/1975 | Collins et al................. | 260/45.75 S |

*Primary Examiner*—Helen M. S. Sneed

[57] ABSTRACT

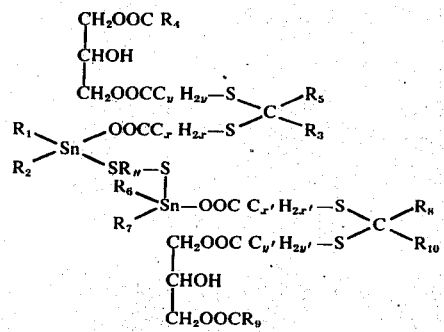

where $x$, $x'$, $y$ and $y'$ are 1 – 6, $R_1$, $R_2$, $R_6$ and $R_7$ are $C_{1-12}$ alkyl, cycloalkyl, aromatic or aralkyl hydrocarbyl, $R_4$ and $R_9$ are as defined for $R_1$ or are $C_{13-21}$ alkyl, $C_{2-20}$ alkenyl or substituted aromatic hydrocarbyl, $R_3$, $R_5$, $R_8$ and $R_{10}$ are as defined for $R_4$ or are hydrogen or a pair of $R_3$ and $R_5$ or $R_8$ and $R_{10}$ together with the carbon atom to which they are joined form a cycloalkyl ring and $R_{11}$ is an aliphatic radical of 2–12 carbon atoms having CH and optionally O and/or S in COC,

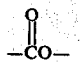

or —CSC— groups, or optionally substituted cyclohexylene or phenylene.

27 Claims, No Drawings

ORGANOTIN COMPOUNDS

The present invention relates to organotin compounds and to their use as stabilizers for polymeric materials, in particular halogenated resins such as polymers and copolymers of vinyl chloride and vinylidene chloride.

The use of organotin compounds containing sulphur as stabilizers for halogenated resins has for many years been recognised as being highly effective. However, the compounds employed have normally been those having a comparatively high tin content and so, in view of the high cost of tin, are expensive relative to other available stabilisers. Thus, despite their high efficiency these compounds are still not as widely used as other, less effective, materials.

The compounds of the present invention are sulphur-containing organotin compounds which have a lower tin content than most conventional sulphur-containing organotin compounds and so are potentially cheaper. The stabilising ability of some of them may match that of some of the conventional materials and so may be able to achieve the same degree of stabilisation for lower cost.

Accordingly, the present invention provides new chemical compounds of the formula:

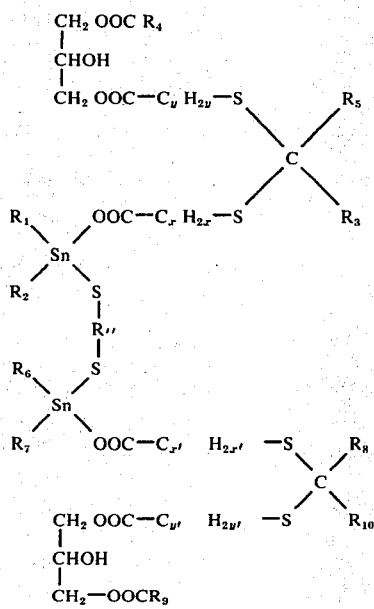

wherein each of $R_1$, $R_2$, $R_6$ and $R_7$ which may be the same or different is a $C_{1-12}$ alkyl group, cycloalkyl group, aromatic hydrocarbyl group, eg. of 6 to 19 carbon atoms, eg. phenyl or aralkyl hydrocarbon group of 7 to 19 carbon atoms, such as benzyl, each of $R_4$ and $R_9$, which are the same or different, is as defined above for $R_1$, $R_2$, $R_6$, and $R_7$ or is an alkyl group of 13 to 21 carbon atoms, an alkenyl group of 2 to 20 carbon atoms or a substituted aromatic hydrocarbon group, (eg. a substituted phenyl group), wherein the substituent is preferably at least one group of formula —OH, —OR$_4$, —SR$_4$, —COOR$_4$, —OOCR$_4$ or —SSR$_4$, each of $R_3$, $R_5$, $R_8$ and $R_{10}$ which are the same or different, is as defined above for $R_4$ and $R_9$, or is hydrogen or at least one of the pairs $R_3$ and $R_5$, and $R_8$ and $R_{10}$ together with the carbon atom to which they are attached forms a cyclo alkyl ring, preferably a cyclohexane or cyclopentone ring, each of $x$, $x'$, $y$ and $y'$ which are the same or different, is an integer of 1 – 6, $R_{11}$ is an aliphatic radical of 2 – 12 carbon atoms consisting of C and H and optionally O and/or S atoms in C—O—C,

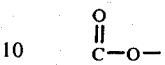

or C—S—C groups, or optionally substituted cyclohexylene or phenylene group, the optional substituents in the cyclohexylene or phenylene groups being inert and for example alkyl of 1 to 4 carbons or halogen, eg. chlorine.

Preferably the compounds are symmetric with $R_1$, $R_2$, $R_3$, $R_4$, $R_5$, $x$ and $y$ the same respectively as $R_6$, $R_7$, $R_8$, $R_9$, $R_{10}$, $x'$ and $y'$. $R_1$, $R_2$, $R_6$ and $R_7$ are preferably alkyl of 4 to 8 carbon atoms, eg. n-butyl or n-octyl groups, or cycloalkyl groups of 5 – 7 carbon atoms, eg. cyclohexyl groups, $R_5$ and $R_{10}$ are preferably hydrogen or methyl groups, $R_4$ and $R_9$ are normally alkyl or alkenyl groups each of 10 to 19 carbon atoms, preferably linear ones, eg. of 17 carbon atoms, $R_3$ and $R_8$ are preferably phenyl or substituted phenyl where the substituent is preferably alkyl or alkoxy each of 1 to 6 carbon atoms, eg. methyl or methoxy, or hydroxyl (for example p-methyl phenyl or O-hydroxyphenyl), branched chain alkyl groups of 3 to 10, preferably 4 to 8 carbon atoms, and preferably those in which the free valency is at the point of branching, ie. of formula —CH $R_{12}R_{13}$ where $R_{12}$ and $R_{13}$ are alkyl groups of 1 to 6 carbon atoms, eg. pent - 3 - yl and hept - 3 - yl groups, or straight chain alkyl groups of 7 to 13 carbon atoms, eg. n-nonyl groups, $x$ and $x'$ are preferably 1 or 2, and $y'$ and $y$ are preferably 1 or 2.

Preferably $R_{11}$ is an aliphatic group of formula

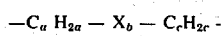

where $b$ is 0 or 1, X is oxygen, sulphur or an aliphatic group comprising an ester group such as a —COO— group or one of formula

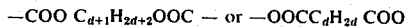

each of $a$ and $c$, which are the same or different, is an integer of 1 to 6, $d$ is 0 or an integer of 1 to 6, such that the sum of $a + c + d$ is not more than 12, and $a$ or $c$ respectively are not 1 when the $C_aH_{2a}$ or $C_cH_{2c}$ group respectively is bonded directly to oxygen. Usually $R_{11}$ is linear. When $b$ is 0, $a$ and $c$ are 1 – 6 and often 1 – 3. When $b$ is one, $a$ and $c$ are preferably 1 – 3, X is preferably oxygen or an ester of formula —COOC$_{d+1}$H$_{2d+2}$OOC— and $d$ is 1.

Examples for $R_{11}$ are , α,ω-alkylene, especially 1,6-hexylene, 1,12-dodecylene and 1,2-ethylene, oxy bis (ethylene), decylene and the group of formula —CH$_2$COOCH$_2$CH$_2$OOCCH$_2$—. Another example of $R_{11}$ is ethylcyclohexylene.

The groups $C_xH_{2x}$, $C_{x'}H_{2x'}$, $C_yH_{2y}$ and $C_{y'}H_{2y'}$ are preferably linear, eg. of formula $(CH_2)_x$.

In preferred compounds of formula 1, the groups

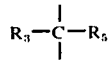

and

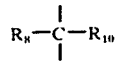

are the same and represent groups of formula

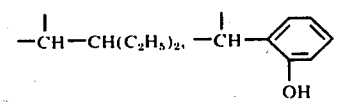

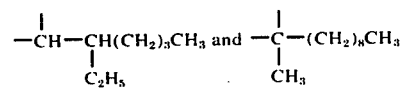

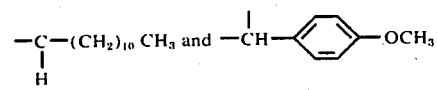

The present invention also provides a process for preparing the compounds of the invention by reacting a precursor of formula II

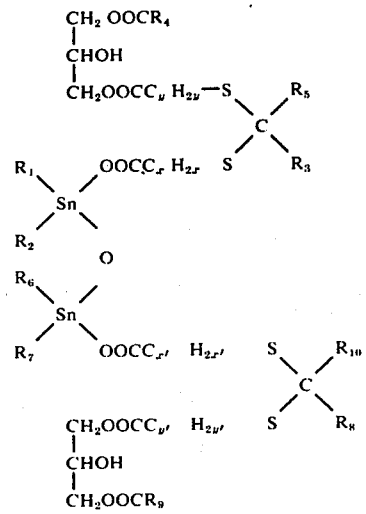

with a dithiol of formula $HSR_{11}SH$. Usually about equimolar amounts of the reagents are used and the reaction is carried in a hydrocarbon solvent, eg. an aromatic hydrocarbon solvent such as xylene or toluene, under reflux conditions with removal of the water produced by the reaction, eg. via a Dean and Stark trap.

The precursors of formula II and their production are described in our German Patent Application OLS No. 2,359,346. They are made by reacting an intermediate of formula III

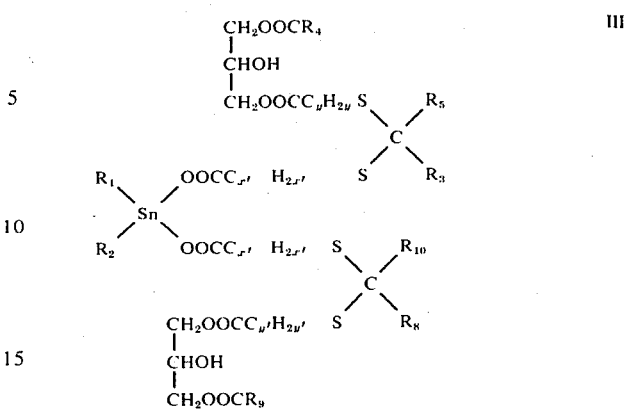

with an oxide of formula $R_6R_7SnO$; usually about equimolar amounts of the reactants are used. The intermediates of formula III and their production are also described in German Application OLS No. 2,359,346.

The intermediates of formula III can also be reacted directly with a dithiol of formula $HSR_{11}SH$ to produce the compounds of the invention, if at least two moles of the intermediate per mole of thiol are present. The reaction is usually carried out in a concentrated liquid phase, eg. one with at least 20% by weight, usually 20 – 50% by weight of organotin compound of formula III. The high concentration helps to minimize formation of compounds of formula

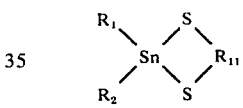

The intermediates of formula III can be prepared by reacting at least one mole of a mono ester of glycerol of formula $HOCH_2\ CHOH\ CH_2OCOR_4$ with one mole of a mercapto carboxylic acid of formula $HS\ C_yH_{2y}\ COOH$ to produce an intermediate of formula $HS\ C_yH_{2y}\ COO\ CH_2CHOH\ CH_2OCO\ R_4$, reacting this intermediate with a carbonyl compound of formula $R_3R_5CO$ and a mercapto carboxylic acid of formula $HSC_xH_{2x}\ COOH$, the intermediate, carbonyl compound and latter mercapto carboxylic being used in about equimolar amounts, and then reacting the product with half a mole or less of a tin oxide of formula $R_1R_2SnO$.

It is convenient to carry out the preparation of the intermediates of formula III and their subsequent conversion to compounds of formula I either directly or via precursors of formula II all in the same reaction solvent, without isolation except for the compound of formula I. The solvent may be a hydrocarbon, such as an aromatic hydrocarbon, eg. benzene, toluene or xylene, an aliphatic hydrocarbon, eg. a light petroleum bp<100° C or hexane or a cycloaliphatic hydrocarbon, eg. cyclo-hexane. Frequently it will also be desirable to have an acidic catalyst present, such as p-toluene sulphonic acid, hydrochloric acid or a metal chloride suitable as a Friedel - Crafts catalyst, such as zinc chloride.

Compounds according to the invention find use as stabilisers for halogen-containing resins, that is for polymers or copolymers of vinyl chloride or vinylidene chloride, chlorinated vinyl chloride polymers and chlorinated polyethylene. Accordingly, from a further aspect the present invention provides a composition which comprises a halogen-containing resin and as a stabiliser therefore a compound of the formula I.

The organotin compounds will be present in compositions according to the invention in amounts so as to produce the desired stabilising effect; often this will be from 0.01–10%., preferably 0.2 – 5%, and especially 2 – 3% by weight based on the total amount of polymeric resin present. It has also been found that by mixing 1 – 50% by weight (based on the weight of the organotin compound of the invention) of a monoalkyltin compound such as a monoalkyltin tris thioglycollate ester of an alkanol of 1 to 20 carbon atoms, eg. monobutyltin tris (iso-octyl thioglycollate) with the organotin compound, the stabilizing efficiency of the compound increases. Monoalkyltin compounds with 1 to 10 carbon atoms, especially 4 – 8 carbon atoms in the alkyl group phosphite and trioctyl phosphite. Diesters of phosphorous acid such as di-isopropyl phosphite, dibutyl phosphite and diphenyl phosphite are also of use. Particularly preferred, however, are the mixed alkyl aryl phosphites such as octyl diphenyl phosphite, isodecyl diphenyl phosphite and di-isodecyl phenyl phosphite. The effect of the mixed phosphites may also be obtained by employing a mixture of a triaryl phosphite and an alcohol in conjunction with the organotin compound. A particularly suitable mixture is that of triphenyl phosphite and isodecanol.

The stabiliser composition is also useful if it is employed in a polymer composition containing an epoxy compound, as may be desired, for example in cases where a delay of initial colour change is desired. Epoxy compounds which may be employed in such compositions include butyl epoxy stearate, esters of epoxidised eleic acid and compounds of the formula.

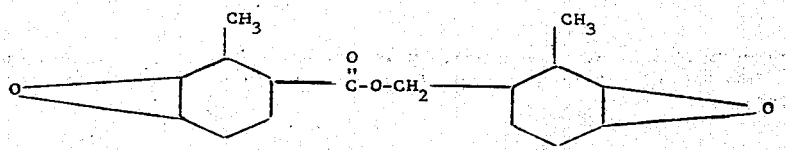

are preferred. Preferably 5 – 25% based on total amount of organotin compound is used. Other additives which also improve the initial clarity of polymer during thermal tests with organotin compounds are:
 a. Butyl epoxy stearate (B.E.S.)
 b. Dibutyltin sulphide and oxide
 c. Dibutyltin cyclic mercapto acetate and/or Dibutyltin cyclic $\beta$-mercapto propionate and/or Dioctyltin cyclic mercapto acetate and/or Dioctyltin cyclic $\beta$-mercapto propionate.

Optionally, but advantageously, compositions according to the invention also contain as auxiliary stabilizers hindered phenols, that is those having at least one alkyl substituent in a position ortho to the hydroxyl group, and preferably an alkyl group in both ortho positions. Such phenols which are of use in compositions of the present invention include butylated hydroxyanisole, 2,6-di-tert.-butylphenol, methylene bis-(2,4-di-tert.-butylphenol), methylene bis-(2,6-di-tert.-butylphenol), methylene bis-(2,6-di-tert.-butyl-3-methylphenol), 4,4'-butylidene bis(6-tert.-butyl-3-methylphenol), methylene bis-(4-ethyl-6-tert.-butylphenol), methylene bis-(4-methyl-2,6-di-tert.-butylphenol). Particularly preferred, however, is 2,6-di-tert.-butyl-4-methyl phenol.

Such phenols may be present in an amount of up to 3%, preferably from 0.01 to 0.05% by weight of the resin and will normally be present at about 4 – 10% by weight, preferably 5 – 8% based on the total amount of organotin compounds used.

Esters of phosphorous and thiophosphorous acid may be employed in compositions according to the invention. Such compounds include halo-phosphites such as tris chloropropyl phosphite and polymeric phosphites such as those from hydrogenated 4,4'-isopropylidene diphenol. Preferred phosphites and thiophosphites, however, are monomers having no substituents in the organo-group and having no more than one sulphur atoms. These include triaryl phosphites and trialkyl phosphites. Such compounds include, for example, triphenyl phosphite, trixylylphosphite, trinonyl phenyl Organotin formulations as described above, optionally including a hindered phenol, an alkyl aryl phosphite or aryl phosphite or an epoxide, will often be used as the only stabiliser in a polymeric vinyl chloride or vinylidene chloride compositions. However, if desired conventional thermal stabilisers may also be included. These may include, for example, metal soap stabilisers, such as cadmium, barium or zinc salts of fatty acids, or lead salts such as lead carbonate or stearate or dibasic lead phosphite or phthalate, or tribasic lead sulphate or conventional organotin stabilisers, such as dibutylin dilaurate or dibutyltin maleate or sulphur-containing compounds such as dibutyltin bisthioglycollates.

In the practice of the invention the stabiliser formulation may be mixed with the copolymer resin in the conventional manner, for example by milling with the resin on heated rolls at 100°–160° C eg. about 150° C, although higher temperatures may be used when convenient, or by being mixed with particles of the polymer and then melting and extruding the mixture, or by adding the stabiliser to a liquid resin.

Resins which may be used in compositions according to the invention normally contain at least 40% by weight of chlorine. Usually it will be a polymer or copolymer of vinyl chloride or vinylidene chloride but post-halogenated polyvinyl chloride or post-halogenated polyolefines, such as polyethylene, may be employed if desired. Suitable monomers which may form such copolymers with vinyl chloride and vinylidene chloride include for example acrylonitrile, vinyl acetate, methyl methacrylate, diesters of fumaric acid and maleic acid, ethylene, propylene and lauryl vinyl ether and these co-monomers may be present in an amount of up to 25% of the total weight of monomers copolymerised.

The organotin stabiliser formulation may be employed in either plasticised resin compositions, for example those plasticised with carboxylic ester plasticisers, eg. di-2-ethylhexyl phthalate, dibutyl sebacate or di-isooctyl phthalate or with phosphate esters such as tri-(alkyl phenyl) phosphates or may be employed in rigid compositions. Such rigid compositions contain little or no plasticisers although for some applications up to about 10% by weight of plasticiser may be present. This is in contrast with plasticised compositions where the amount of plasticisers present is normally greater than 50% by weight of the polymeric material, and is often greater than 100% on that basis; amounts of 30 – 150% are often used.

In addition to the stabilisers, the compositions of the invention may also contain conventional additives, eg. pigments, fillers, dyes and ultraviolet absorbing agents.

The invention is illustrated in the following Examples;

EXAMPLE 1

Glycerol mono stearate (34.8g., 0.1 M) and β-mercaptopropionic acid (10.6g., 0.1 M) were refluxed in toluene (250 ml) in the presence of p-toluene sulphonic acid (Ca. 0.2g. – 0.3g.) till the calculated amount of water had collected [to give $C_{17}H_{35}$ COOCH$_2$ —CH(OH)—-CH$_2$OOC CH$_2$CH$_2$SH] 2 - Ethyl butyraldehyde (10.0g., 0.1 M) and β-mercaptopropionic acid (10.6g., 0.1 M) were also added into the above warm solution, and the mixture refluxed until the calculated amount of water had collected again

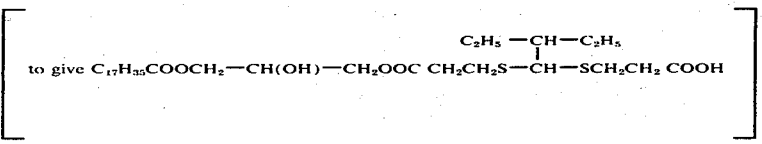

Dibutyltin oxide (12.5g., 0.05 M) was also added into the above warm solution and the mixture refluxed as above

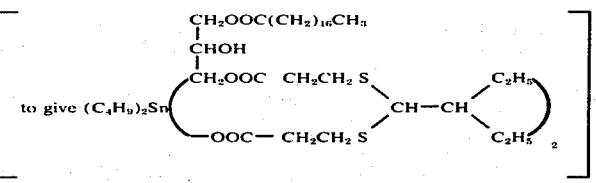

The solution was cooled, dibutyltin oxide (12.5 g., 0.05M) was further added thereto and the mixture refluxed until a clear solution was obtained to give

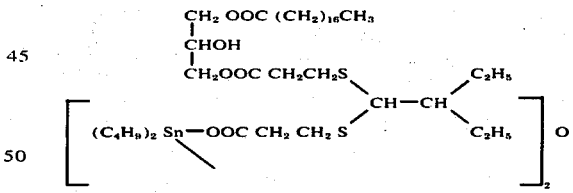

Finally 1,6-Hexane dithiol (7.5g.) was added dropwise via a separating funnel into the above warm solution and the mixture refluxed until the calculated amount of water had collected (denoting completion of reaction). The hot solution was then filtered under vacuum and the toluene was removed from the warm solution under reduced pressure to leave the product as a white soft waxy solid at room temperature.

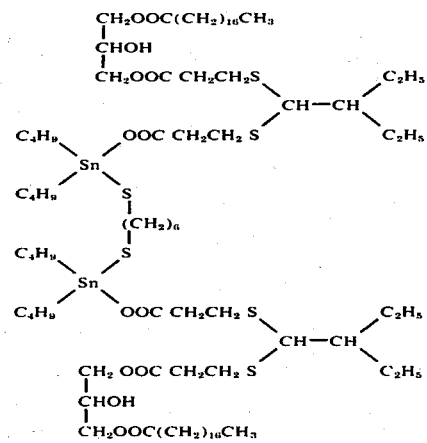

| Analysis | Calculated | Found |
|---|---|---|
| | Sn = 12.6% | Sn = 12.6% |
| | S = 10.2% | S = 10.5% |
| | C = 56.2% | C = 56.12% |
| | H = 9.0% | H = 9.2% |

EXAMPLE 2

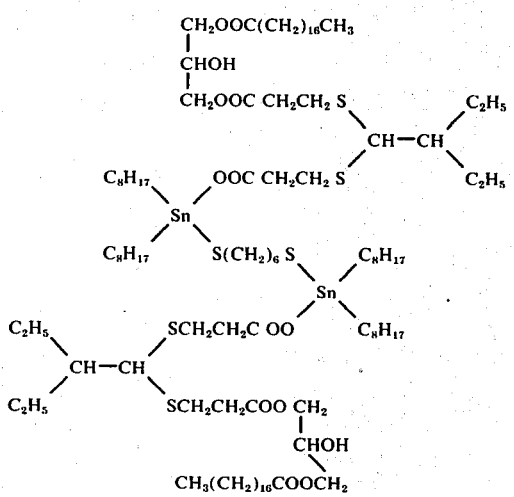

This compound was prepared by the same method as in Example 1 using 18.0g. of dioctyltin oxide each time to replace each 12.5g. of dibutyltin oxide used in that Example.

The product is a white waxy solid at room temperature.

| Analysis | Calculated | Found |
|---|---|---|
| | Sn% = 11.3 | Sn% = 10.7 |
| | S% = 9.1 | S% = 9.2 |
| | C% = 59.3 | C% = 58.02 |
| | H% = 10.0 | H% = 9.64 |

Its structure was also confirmed by I.R. and N.M.R. analysis.

EXAMPLE 3

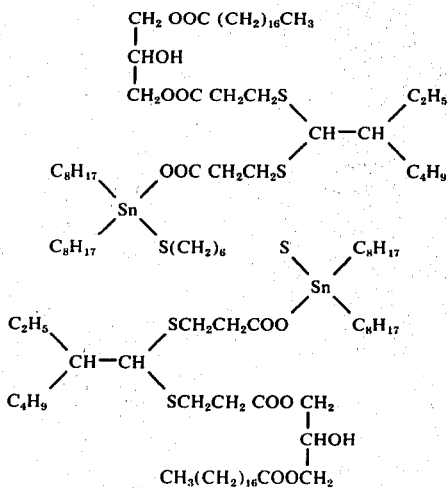

This compound was prepared by the same method as in Example 2 using 12.8g. of 2-ethylhexanal instead of 10.0g. of 2-ethyl butyraldehyde.

The product is a light yellow waxy solid at room temperature.

| Analysis | Calculated | Found |
|---|---|---|
| | Sn = 11.0% | Sn = 11.0% |
| | S = 8.8% | S = 8.4% |
| | C = 60.0% | C = 60.2% |
| | H = 9.7% | H = 9.7% |

Its structure was also confirmed by N.M.R. analysis.

EXAMPLE 4

Polyvinyl chloride resins containing compounds of Examples 1 – 3 were tested for initial colour development against known stabilisers. Improved results were obtained in spite of the lower tin content of the compounds of the invention as compared to the known stabilizers (see Table 1).

The known stabilizers were dibutyltin bis(iso-octyl tioglycollate), (stabilizer A), dioctyltin bis(iso-octyl thioglycollate), (stabilizer B), and a mixture of stabilizer B with 5% of dioctyltin cyclic mercaptoglycollate (stabilizer C).

A series of rigid (non - plasticized) formulations were prepared from the polyvinyl chloride resin Corvic D55/09 (100 parts). When testing the compounds of the invention lubricant has not been added to the polymer because the new compounds tested themselves act as a lubricant during milling at about 155° C, but with known stabilizers 0.5 parts of Lubricant (Laurex CS) (per 100 parts of Polymer) has been added, (marked * in Table 1).

TABLE 1

| Test | Stabilizer(s) | Total parts of stabilizers in 100 parts of P.V.C. | Colour on Gardner Scale after heating at 190° C for given time in mins. | | |
|---|---|---|---|---|---|
| | | | 0 | 5 | 5½ | 10 |
| 1 | (a) * A | 1.5 | 0 | — | 3 | 5 |
| | (b) Product Ex. 1 | 0.9 | 0 | — | 0 | 2 |
| | (c) Product Ex. 1 | 0.7 | 0 | — | 0 | 3+ |
| | (d) Product Ex. 1 | 0.5 | 0 | — | 0 | 5– |
| 2 | (a) * B | 1.5 | 0 | 4 | — | 6 |
| | (b) Product Ex. 2 | 1.5 | 0 | 0 | — | 1–2 |
| 3 | (a) * B | 1.0 | 0 | 3+ | — | 6 |
| | (b) Product Ex. 3 | 1.0 | 0 | 0 | — | 3– |
| | (c) * C | 1.0 | 0 | 0 | — | 4+ |

We claim:
1. An organotin compound of the general formula

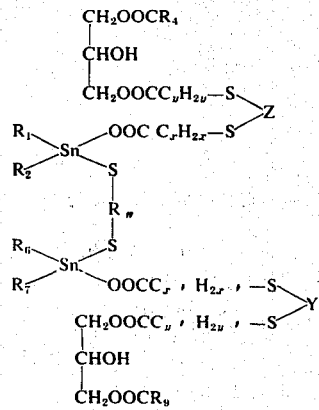

wherein Z is selected from the group consisting of a group of formula

and a group of formula

Y is selected from the group consisting of a group of formula

and a group of formula

$x$, $x'$, $y$ and $y'$ are each selected from the group consisting of integers of 1 – 6, $R_1$, $R_2$, $R_6$ and $R_7$ are each selected from the group consisting of alkyl groups of 1 to 12 carbon atoms, cycloalkyl groups, aromatic hydrocarbyl groups and aralkyl hydrocarbyl groups, $R_4$ and $R_9$ are each selected from the group consisting of alkyl groups of 1 – 21 carbon atoms, alkenyl groups of 2 to 21 carbon atoms, cycloalkyl groups, aromatic hydrocarbyl groups and aralkyl hydrocarbyl groups, $R_3$, $R_5$, $R_8$ and $R_{10}$ are each selected from the group consisting of alkyl groups of 1 to 21 carbon atoms, alkenyl groups of 2 to 21 carbon atoms, cycloalkyl groups, aromatic hydrocarbyl groups and aralkyl hydrocarbyl groups and hydrogen, $R_{11}$ is selected from the group consisting of divalent aliphatic groups of 2 to 12 carbon atoms consisting of atoms selected from the group consisting of C and H atoms, C, H, and O atoms, C, H and S atoms, and C, H, O, and S atoms, said O or S atoms being in —C—O—C, —C—S—C— or

links, cyclohexylene groups or phenylene groups, and each of $R_{14}$ and $R_{15}$ is an alkylene group of 4 to 6 carbon atoms.

2. A compound according to claim 1 where the aromatic hydrocarbyl group represented by at least one of $R_4$, $R_9$, $R_3$, $R_5$, $R_8$ and $R_{10}$ has at least one nuclear substituent which is selected from the group consisting of hydroxyl and alkoxyl groups of 1 to 6 carbon atoms.

3. A compound according to claim 1 wherein $R_{11}$ is selected from the group consisting of cyclohexylene groups with at least one substituent which is an alkyl group of 1 to 4 carbon atoms or a halogen atom and phenylene groups with at least one substituent which is an alkyl group of 1 to 4 carbon atoms or a halogen atoms.

4. A compound according to claim 1 wherein $R_{11}$ is an aliphatic group of formula

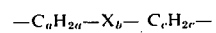

where $b$ is 0 or 1, X is oxygen or sulphur or an ester group of formula

—COO $C_{d+1}$ $H_{2d+2}$ OOC— or —OOC $C_d$ $H_{2d}$ COO—, each of $a$ and $c$, which are the same or different, is an integer of 1 to 6, such that the sum of $a + c + d$ is not more than 12, and $a$ or $c$ is not 1 when the —$C_aH_{2a}$ or $C_c H_{2c}$ group respectively is bonded directly to oxygen.

5. A compound according to claim 4 wherein $b$ is 0 and $a$ and $c$ are 1 – 6.

6. A compound according to claim 5 wherein $R_{11}$ is a 1,6- hexylene, 1,12- dodecylene or 1,2- ethylene.

7. A compound according to claim 4 wherein $b$ is 1, $a$ and $c$ are 1 – 3, and X is oxygen or an ester group of formula —COOC$_{d+1}$H$_{2d+2}$OOC—, wherein $d$ is 1 or 2.

8. A compound according to claim 7 wherein $R_{11}$ is an oxy(bis ethylene) group, or is a group of formula —CH$_2$COOCH$_2$CH$_2$OOCCH$_2$—.

9. A compound according to claim 1 wherein each of $x$, $x'$, $y$ and $y'$ is 1 or 2.

10. A compound according to claim 1 wherein $R_1$, $R_2$, $R_3$, $R_4$, $R_5$, $x$ and $y$ are the same respectively as $R_6$, $R_7$, $R_8$, $R_9$, $R_{10}$, $x'$ and $y'$.

11. A compound according to claim 1 wherein each of $R_1$ $R_2$ $R_6$ and $R_7$ is an alkyl group of 4 to 8 carbon atoms or a cycloalkyl group of 5 to 7 carbon atoms.

12. A compound according to claim 1 wherein each of $R_5$ and $R_{10}$ is hydrogen or an alkyl group of 1 to 6 carbon atoms.

13. A compound according to claim 1 wherein each of $R_4$ and $R_9$ is an alkyl group of 10 to 19 carbon atoms or an alkenyl group of 10 to 19 carbon atoms.

14. A compound according to claim 1 wherein each of $R_3$ and $R_8$ is a phenyl group; a substituted phenyl group with at least one substituent, which is an alkyl group of 1 to 6 carbon atoms, an alkoxy group of 1 to 6 carbon atoms, or a hydroxy group; a branched chain alkyl group of 3 to 10 carbon atoms or a straight chain alkyl group of 7 to 13 carbon atoms.

15. A compound according to claim 12 wherein the groups

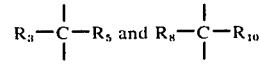

are the same and represent groups of formula $-\overset{|}{C}H-CH(C_2H_5)_2, \ -\overset{|}{C}H-\underset{\underset{C_2H_5}{|}}{CH}(CH_2)_3CH_3,$

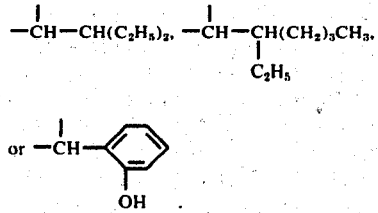

16. A compound according to claim 5 wherein $R_1$, $R_2$, $R_6$ and $R_7$ are the same and are n-butyl or n-octyl groups, $R_3$ and $R_8$ are the same and are phenyl, hydroxyphenyl, or alkoxyphenyl groups or branched chain alkyl groups of 3 to 10 carbon atoms or straight chain alkyl groups of 7 to 13 carbon atoms, $R_4$ and $R_9$ are alkyl groups of 10 to 19 carbon atoms or alkenyl groups of 10 to 19 carbon atoms, $R_5$ and $R_{10}$ are the same and are hydrogen or methyl, $x, x', y$ and $y'$ are the same and are 1 or 2, and $R_{11}$ is $\alpha,\omega$-alkylene of 2 to 12 carbon atoms.

17. A compound according to claim 16 of the formula

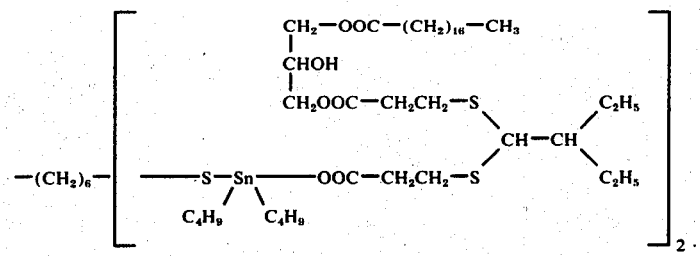

18. A claim according to claim 16 of the formula

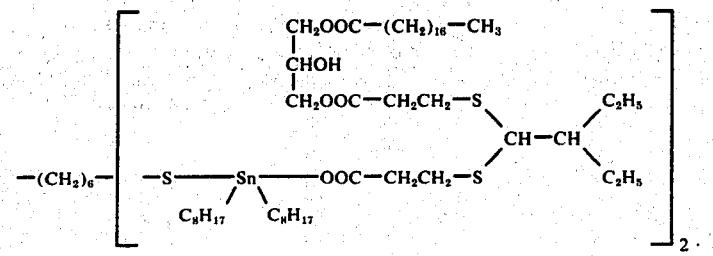

19. A compound according to claim 16 of the formula

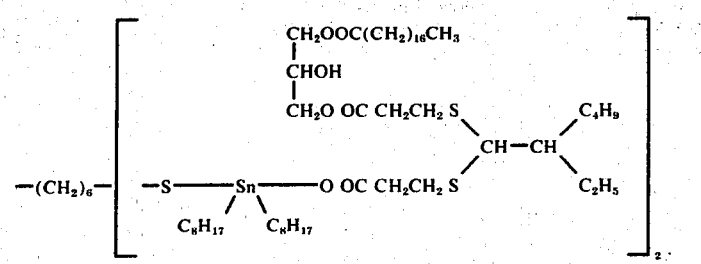

20. A process for preparing an organotin compound as claimed in claim 1, which comprises reacting an intermediate of formula

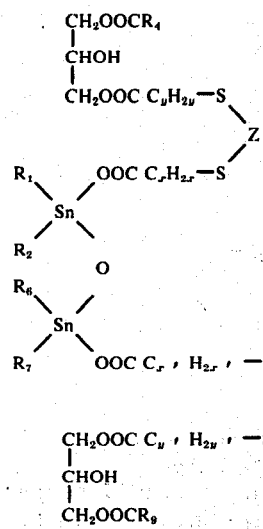

with a dithiol of formula $HSR_{11}SH$, wherein each of $R_1$–$R_{11}$ $Y, Z, x, x', y$ and $y'$ is defined in claim 1.

21. A process according to claim 20 which the intermediate is prepared by reacting a precursor of formula

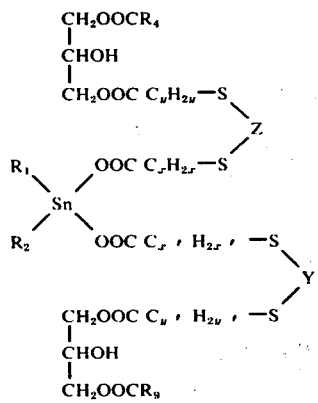

with an oxide of formula $R_6R_7SnO$.

22. A process according to claim 21 wherein the precursor is prepared by reacting a compound of formula

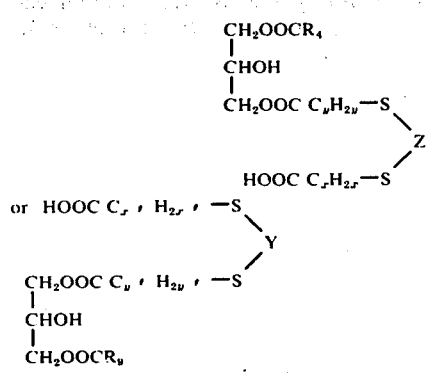

with at least one tin compound of formula $R_1R_2SnO$, $R_1R_2SnS$, $R_6R_7SnO$ or $R_6R_7SnS$, the molar ratio of tin compound to total precursors being 0.5:1 or less.

23. A process according to claim 20 wherein the intermediate is prepared by reacting a tin free compound of formula

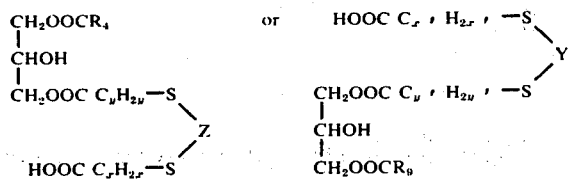

with at least one tin compound selected from the group consisting of compounds of formula $R_1R_2SnO$, and $R_6R_7SnO$, the total molar ratio of tin compounds to tin free compounds being at least 1:1.

24. A process according to claim 23 wherein the tin free commmpound is prepared by reacting at least one molar proportion of a mono ester of glycerol of formula HO $CH_2CHOH$ $CH_2OCOR_4$ with one molar proportion of a mercapto carboxylic acid of formula HS $C_yH_{2y}COOH$ to produce an intermediate of formula HS $C_yH_{2y}COOCH_2CHOH$ $CH_2OCOR_4$, reacting this intermediate with a carbonyl compound of formula ZO and a mercapto carboxylic acid of formula HS $C_xH_{2x}COOH$ to produce the said precursor, the intermediate, carbonyl compound and latter mercapto carboxylic acid being reacted in about equimolar proportions.

25. A process for preparing an organotin compound as claimed in claim 1 which comprises reacting a compound of formula

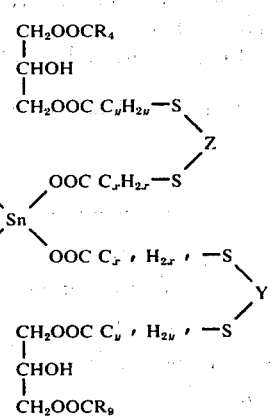

with a dithiol of formula $HSR_{11}SH$ in a molar ratio of at least 2:1, wherein each of $R_1$ to $R_{11}$, Y, Z, $x$, $x'$, $y$ and $y'$ is as defined in claim 1.

26. A polymeric composition comprising a halogen containing resin and as stabilizer therefore 0.01 – 10% by weight of an organotin compound as claimed in claim 1.

27. A composition according to claim 26 which comprises polyvinyl chloride and 0.2 – 5% by weight of said organotin compound.

* * * * *